United States Patent [19]
Joo et al.

[11] Patent Number: 6,156,932
[45] Date of Patent: Dec. 5, 2000

[54] PREPARATION OF 4,4'-DINITRODIPHENYLAMINE FROM UREA AND NITROBENZENE

[75] Inventors: Young J. Joo; Jin-Eok Kim; Jeong-Im Won; Kum-Ui Hwang, all of Taejeon, Rep. of Korea

[73] Assignee: Korea Kumho Petrochemical Co., Ltd., Seoul, Rep. of Korea

[21] Appl. No.: 09/511,281

[22] Filed: Feb. 23, 2000

[51] Int. Cl.$^7$ .................................................. C07C 209/00
[52] U.S. Cl. .............................................................. 564/414
[58] Field of Search ............................................. 564/414

[56] References Cited

U.S. PATENT DOCUMENTS 4,990,673  2/1991  Tronich et al. .
5,233,010  8/1993  Stern et al. .
5,453,541  9/1995  Stern et al. .

*Primary Examiner*—Samuel Barts
*Attorney, Agent, or Firm*—Harrison & Egbert

[57] ABSTRACT

A method for preparing 4,4'-dinitrodiphenylamine, including reacting urea and nitrobenzene in a polar organic solvent in the presence of a base at a temperature of room temperature to 100° C. The method employs a relatively cheap urea and nitrobenzene as the raw materials, and also employs a relatively cheap base, thereby decreasing the manufacturing costs. Moreover, the method does not produce by-products, thus eliminating a need for a post-treating process. Additionally, the method is advantageous in that the production of 4,4'-dinitrodiphenylamine can be achieved in high yield and selectivity even under non-intensive reaction conditions by appropriately controlling the amounts of urea and nitrobenzene.

7 Claims, No Drawings

PREPARATION OF 4,4'-DINITRODIPHENYLAMINE FROM UREA AND NITROBENZENE

TECHNICAL FIELD

Field of the Invention

The present invention relates in general to a method of preparing 4,4'-dinitrodiphenylamine by reacting urea and nitrobenzene in a polar organic solvent in the presence of an organic or inorganic base. More particularly, the present invention relates to a method of selectively preparing 4,4'-dinitrodiphenylamine by dissolving urea and nitrobenzene in a polar organic solvent, and then by allowing the urea and nitrobenzene to react together in the resulting solution while using an inorganic base, such as sodium hydroxide, or an organic base, such as tetramethylammonium hydroxide (hereinafter, called "TMA(OH)").

BACKGROUND ART

Because 4,4'-dinitrodiphenylamine is easily reduced into 4,4'-diaminodiphenylamine, it is mainly used as a raw material for an antioxidant for a dye or rubber. Japanese Patent Publication No. Heisei 10-168038 (1998) describes a method for synthesizing diaminodiphenylamine such synthesizing method involving a reduction of dinitrodiphenylamine. In the above mentioned patent publication, a diaminodiphenylamine compound is described as being highly effective as an intermediate of an antioxidant or antiaging agent. 4,4'-diaminodiphenylamine or its derivatives, besides being used as an intermediate of an additive to rubber, are also used as an intermediate of dyes, agricultural chemicals and medical substances.

An example of conventional methods for preparing 4,4'-dinitrodiphenylamine involves nitration and deacetylation of N-acetyldiphenylamine. Such a method, however, is problematic in that the nitration is non-uniformly carried out. Furthermore, there is an inconvenience in that the nitrodiphenylamine inevitably produced is removed using a recrystalization from alcohol. With another method for preparing 4,4'-dinitrodiphenylamine, U.S. Pat. No. 4,990,673 (1991) discloses a method in which 4-chloroaniline is reacted with alkali metal cyanate to produce 4,4'-dinitrodiphenylamine. However, a disadvantage with this method is that the reaction must be carried out at a temperature of 160° C. or above for an extended period of time of more than 15 hours.

In addition, another method of preparing the dinitrodiphenylamine derivative is the reaction of 4-nitroaniline with a nitrobenzene derivative (see, J. Am. Chem. Soc., 1976, (1), pp 138–143). Such a reference describes a method in which 4-nitroaniline and nitrobenzene derivatives are allowed to react using potassium t-butoxide (t-BuOK) as a base, thereby producing 2,4¹-dinitrodiphenylamine or 4,4'-dinitrodiphenylamine depending on the amount of the base, or alternatively producing 5-chloro (bromo)-2,4'-dinitrodiphenylamine using halogen as a substitute.

The present invention relates to a method of selectively preparing 4,4'-dinitrodiphenylamine using a nucleophilic aromatic substitution for hydrogen (hereinafter, called "NASH"). The NASH reaction recently proposed is advantageous in that, since amine or amide is reacted directly with nitrobenzene or its derivative in the presence of a base, any hazardous material or any intermediate, which is difficult to be removed, is not produced.

A process is also known wherein aniline and nitrobenzene are directly reacted in the presence of a base, such as "TMA(OH)", to prepare 4-nitrodiphenylamine (hereinafter, called "4-NDPA") and 4-nitrosodiphenylamine. See, J. Am. Chem. Soc., 1992, 114(23), 9237–8; U.S. Pat. No. 5,117,063; U.S. Pat. No. 5,253,737; U.S. Pat. No. 5,331,099; U.S. Pat. No. 5,453,541; U.S. Pat. No. 5,552,531; and U.S. Pat. No. 5,633,407.

In addition, the use of the NASH reaction is described in U.S. Pat. No. 5,436,371, U.S. Pat. No. 5,117,063, and International Patent Publication No. WO 93/24447. These patents disclose a method of synthesizing N-(4-nitrophenyl) benzamide using benzamide rather than aniline. More concretely, prior art describes preparing 4-nitroaniline by synthesizing N-(4-nitrophenyl)benzamide using nitrobenzene in the amount of about 1 mole based on benzamide and then by hydrolyzing the resulting product with water or ammonia. However, there is no mention of the preparation of 4,4'-nitrodiphenylamine. This seems to be because N-(4-nitrophenyl)benzamide produced by a reaction of amide and nitrobenzene is a stable and separable compound, so that it is no longer reacted with nitrobenzene.

SUMMARY OF THE INVENTION

The present invention employs the NASH reaction as mentioned above, and utilizes urea instead of aniline or benzamide. More particularly, the present invention is a method of selectively preparing 4,4'-dinitrodiphenylamine by reacting urea with an excess of nitrobenzene. 4-Nitroaniline, which is an intermediate produced by the present invention, is increased in production at the beginning of the reaction, and is easily reacted with nitrobenzene to produce 4,4'-dinitrodiphenylamine. The method in accordance with the present invention is advantageous in that the reaction is relatively simple while allowing a selective production of only 4,4'-dinitrodiphenylamine using a relatively cheap alkali base without producing other by-products.

Diligent efforts have been made to find an improved method for preparing 4,4'-dinitrodiphenylamine, which does not involve production of by-products and requirement of any post-treating process. As a result, we have found that 4,4'-dinitrodiphenylamine can be produced without production of by-products and requirement of any post-treating process while reducing the manufacturing costs when urea, which is relatively cheap, is directly reacted with nitrobenzene in a polar organic solvent using a relatively cheap base. It has also been found that the production of 4,4'-dinitrodiphenylamine can be achieved in high yield and selectivity even under non-intensive reaction conditions by appropriately controlling the amounts of urea and nitrobenzene. Based on such facts, the present invention has been achieved.

In accordance with the present invention, an inorganic or organic base may be used for the base existing in the polar organic solvent for the reaction of urea and nitrobenzene to achieve a selective production of 4,4'-dinitrodiphenylamine. Preferably, an alkali metal or alkaline earth metal base, such as sodium hydroxide, may be used for the inorganic base. On the other hand, a base such as TMA(OH) may be preferably used for the organic base. In the reaction of urea and nitrobenzene in accordance with the present invention, 4-nitroaniline is produced at the beginning of the reaction. Using an extended period of reaction time, however, such 4-nitroaniline is reacted with nitrobenzene, thereby producing 4,4'-dinitrodiphenylamine. Consequently, only 4,4'-dinitrodiphenylamine can be obtained without any by-products. 4-Nitroaniline is produced in a fast rate at the beginning of the reaction while reacting with nitrobenzene as the reaction further proceeds, thereby producing only 4,4'-dinitrodiphenylamine. On the other hand, 4,4'-dinitrodiphenylamine is slowly produced at the beginning of the reaction while being produced at an increased rate as the reaction of 4-nitroaniline and nitrobenzene proceeds. The reaction is conducted in such a fashion that it is completed at the point of time when 4-nitroaniline is completely consumed. Moreover, the reaction is carried out under an oxygen atmosphere to prevent azoxybenzene from being produced.

DETAILED DESCRIPTION OF THE INVENTION

The foregoing and other objects, features and advantages of the invention will be apparent to those skilled in the art to which the present invention relates from reading the following specification.

The present invention is directed to a method of selectively preparing 4,4'-dinitrodiphenylamine by reacting urea and nitrobenzene in a polar organic solvent in the presence of an organic or inorganic base.

In the practice of the present invention, dimethylsulfoxide (hereinafter, called "DMSO"), which is a polar organic solvent, is used as the solvent in view of solubilities of urea and nitrobenzene.

The molar ratio of nitrobenzene to urea used is in the range of about 1:1 to about 16:1, with the preferred ratio in view of yield being in the range of about 4:1 to about 8:1. The volume ratio of the solvent to urea and nitrobenzene used is in the range of 50:1 to 1:1, with the preferred ratio being in the range of 30:1 to 1:1.

Examples of the base used in accordance with the present invention include, but are not limited to, organic and inorganic bases, such as sodium hydroxide(NaOH), potassium hydroxide(KOH), potassium t-butoxide(t-BuOK), sodium hydride(NaH), and TMA(OH). The molar ratio of the base to urea used is in the range of about 1:1 to about 20:1. The higher the amount of the base used, the higher the yield. However, where the molar ratio of the base to urea is 12:1 or above, the yield is rather decreased. On the other hand, where the molar ratio of the base to urea is 4:1 or below, results show that 4-nitroaniline remains even when the reaction is carried out at a temperature of 60° C. for 8 hours.

The reaction temperature is in the range of room temperature to 100° C., with the preferred reaction temperature being in the range of 50 to 80° C. Where the reaction temperature is low, such as less than 50° C., the reaction rate is too slow. On the other hand, where the reaction temperature exceeds 80° C., the yield is remarkably decreased due to the decomposition of urea. The lower the reaction temperature, the longer the time during which 4-nitroaniline produced at the beginning of the reaction is converted into 4,4'-dinitrodiphenylamine. Of course, the extended reaction time results in an increase in yield of the product. On the other hand, at the reaction temperature exceeding 80° C., the yield of the product is high at the beginning of the reaction. However, the yield of the product increases no longer from the level at the beginning of the reaction due to a decomposition of urea. Accordingly, the reaction temperature is determined to be ranged from 50° C. to 80° C. in order to prevent a decomposition of urea while increasing the reaction rate, thereby obtaining an increased yield of the product.

Moreover, it was found that, where the moisture content in the reaction system is 5% or less based on the weight of the entire reaction solution, it does not have a significant effect on a reactivity. Thus, no particular process to remove the moisture of the solvent is used. Where the reaction is carried out in a state where water is added to the solvent in an amount of 1%, a high yield is exhibited at the beginning of the reaction. In this case, however, the yield exhibited after the reaction of about 6 hours is not so high, as compared to that of the case where water is not added. In addition, an excess of azoxybenzene is produced under an atmosphere not containing oxygen whereas no azoxybenzene is produced under an atmosphere containing oxygen.

EXAMPLES

The following examples are for illustration purposes only and in no way limit the scope of this invention.

In the following examples, products were analyzed by the Nuclear Magnetic Resonance(NMR) spectrum and the Gas Chromatography-Mass Spectroscopy Detector to identify them. Also, the products were quantitatively analyzed according to the following condition by high performance liquid chromatography (HPLC). Such a high performance liquid chromatography was carried out using a product manufactured by Hitachi Co. in Japan and consisting of an L-6200 intelligent pump and an L-4200 UV-VIS detector. In high performance liquid chromatography, all quantitative values were measured at a wavelength of 254 nm, and developing speed was 1 ml/minute. Furthermore, in high performance liquid chromatography, a Cosmosil 5C18-AR (4.6×150 mm) packed column was used. An elution gradient of high performance liquid chromatography was as follows.

Elution gradient

| Time (minute) | Solvent A % Distilled water | Solvent B % Acetonitrile |
| --- | --- | --- |
| 0 | 65 | 35 |
| 25 | 0 | 100 |
| 33 | 65 | 35 |

For the quantitative analysis of each product, pyrene was used as an internal standard. An area ratio for a concentration of each material was calculated relative to an area of pyrene and standard-calibrated. A molar concentration of a product was calculated from the calibration curve.

Example 1

100 ml three-necked reactor equipped with a condenser and a thermometer was filled with 1.2 g (20 mol.) of urea, 9.6 g (240 mol.) of sodium hydroxide, 0.1 g of pyrene, and 30 ml of DMSO solvent. Then, the resulting mixture was added to 8.2 ml (80 mol.) of nitrobenzene while stirring. Thereafter the resulting solution was stirred for 30 minutes while passing oxygen, so that it was subsequently allowed to conduct a reaction at a temperature of 60° C. A progressed degree of the reaction was confirmed by HPLC. After the reaction, the product was cooled. Analysis of the product by HPLC showed that, where the reaction was carried out for 6 hours, 4,4'-dinitrodiphenylamine was obtained in a yield of 82 mol %, and where the reaction was carried out for 8 hours, 4,4'-dinitrodiphenylamine was obtained in a yield of 94 mol %.

Example 2

Reactions were carried out under the same conditions as those in Example 1 except that the reaction temperature for each reaction was changed. Results are shown in Table 1 below.

TABLE 1

Change in yield with change in reaction temperature

| Reaction temperature (° C.) | Time (hr) | Yield (mol %) 4-NA[A] | Yield (mol %) DNDPA[B] |
|---|---|---|---|
| 60 | 8 | — | 59 |
| 70 | 6 | — | 67 |
| 60 | 6 | — | 82 |
|    | 8 | — | 94 |
| 50 | 6 | 6.9 | 55 |
|    | 8 | 6.8 | 63 |

[A]4-NA: 4-nitroaniline
[B]DNDPA: 4,4'-dinitrodiphenylamine

Example 3

Reactions were carried out under the same conditions as those in Example 1 except that the kind of base and the amount of the base for each reaction were changed. Results are shown in Table 2 below.

TABLE 2

Change in yield with change in the kind of base

| Base | Base amount (g(mol.)) | Time (hr) | Yield (mol %) 4-NA[A] | Yield (mol %) DNDPA[B] |
|---|---|---|---|---|
| Sodium hydroxide | 9.6 (240) | 8 | — | 94 |
| Potassium hydroxide | 17.9 (320) | 8 | 9 | 52 |
| Potassium t-butoxide[C] | 4.5 (40) | 8 | — | 37 |
| TMA(OH)[D] | 8.6 (47) | 8 | — | 51 |

[A]4-NA: 4-nitroaniline
[B]DNDPA: 4,4'-dinitrodiphenylamine
[C]and [D]: 0.6 g (10 mol.) of urea was used.

Example 4

Reactions were carried out under the same conditions as those in Example 1 except that the amount of the base for each reaction was changed. Results are shown in Table 3 below.

TABLE 3

Change in yield with change in the amount of base

| Base amount (g(mol.)) | Reaction time (hr) | Yield (%) 4-NA[A] | Yield (%) DNDPA[B] |
|---|---|---|---|
| 3.2 (80) | 8 | 14 | 55 |
| 6.4 (160) | 8 | 5 | 67 |
| 9.6 (240) | 8 | — | 94 |
| 12.8 (320) | 8 | — | 92 |

[A]4-NA: 4-nitroaniline
[B]DNDPA: 4,4'-dinitrodiphenylamine

Example 5

Reactions were carried out under the same conditions as those in Example 1 except that the amount of DMSO solvent for each reaction was changed. Results are shown in Table 4 below.

TABLE 4

Change in yield with change in the amount of solvent

| Amount of DMSO (ml) | Reaction time (hr) | Yield (%) 4-NA[A] | Yield (%) DNDPA[B] |
|---|---|---|---|
| 20 | 8 | — | 65 |
| 30 | 8 | - | 94 |
| 40 | 8 | 4 | 72 |

[A]4-NA: 4-nitroaniline
[B]DNDPA: 4,4'-dinitrodiphenylamine

Example 6

Reactions were carried out under the same conditions as those in Example 1 except that the amount of nitrobenzene to the amount of urea for each reaction was changed. Results are shown in Table 5 below.

TABLE 5

Change in yield with change in the amount of nitrobenzene

| Amount of nitrobenzene (ml(mol.)) | Reaction time (hr) | Yield (%) 4-NA[A] | Yield (%) DNDPA[B] |
|---|---|---|---|
| 4.1 (40) | 8 | 7 | 67 |
| 8.2 (80) | 8 | — | 94 |
| 16.4 (160) | 8 | — | 75 |

[A]4-NA: 4-nitroaniline
[B]DNDPA: 4,4'-dinitrodiphenylamine

Example 7

Reactions were carried out under the same conditions as those in Example 1 except that moisture content for each reaction were changed. Results are shown in Table 6 below.

TABLE 6

Change in yield with change in moisture content

| Drying agent and moisture content | Reaction time (hr) | Yield (%) 4-NA[A] | Yield (%) DNDPA[B] |
|---|---|---|---|
| None[C] | 8 | — | 94 |
| $K_2CO_3$[D] | 8 | — | 73 |
| 1% Water[E] | 8 | — | 70 |
| 5% Water[F] | 8 | 3 | 58 |

[A]4-NA: 4-nitroaniline
[B]DNDPA: 4,4'-dinitrodiphenylamine
[C]Commercially available solvent was used without further purification (no drying agent was used).
[D]A drying agent was used to remove moisture in a reaction system.
[E]Distilled water was added in the amount of 1% based an the volume of the solvent.
[F]Distilled water was added in the amount of 5% based on the volume of the solvent.

Example 8

Reactions were carried out under the same conditions as those in Example 1 except that an atmosphere for each reaction was changed. Results are shown in Table 8 below.

TABLE 8

Change in yield with reaction atmosphere

| Reaction atmosphere | Reaction time (hr) | Yield (%) | |
|---|---|---|---|
| | | 4-NA[A] | DNDPA[B] |
| Oxygen | 8 | — | 94 |
| Nitrogen | 8 | 2 | 50 |
| Air | 8 | 1 | 75 |
| General atmosphere | 8 | 3 | 56 |

[A]4-NA: 4-nitroaniline
[B]DNDPA: 4,4'-dinitrodiphenylamine

As apparent from the above description, the method of the present invention for preparing 4,4'-dinitrodiphenylamine uses relatively cheap urea and nitrobenzene, as raw materials, while using a relatively cheap base, thereby decreasing the manufacturing costs. Moreover, the method of the present invention does not produce by-products, thus eliminating a need for a post-treating process. Additionally, the method of the present invention is advantageous in that the production of 4,4'-dinitrodiphenylamine can be achieved in high yield and selectivity even under non-intensive reaction conditions by appropriately controlling the amounts of urea and nitrobenzene.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing 4,4'-dinitrodiphenylamine, comprising reacting urea and nitrobenzene in a polar organic solvent in the presence of a base at a temperature of room temperature to 100° C.

2. The method of claim 1, wherein the molar ratio of the nitrobenzene to the urea is in the range of 2:1 to 10:1.

3. The method of claim 1, wherein the molar ratio of the base to the urea is in the range of 1:1 to 20:1.

4. The method of claim 1, wherein the volume ratio of the polar organic solvent to the reactants is in the range of 1:1 to 50:1.

5. The method of claim 1, wherein the base is selected from the group consisting of sodium hydroxide, sodium hydride, potassium hydroxide, potassium t-butoxide, and tetramethylammonium hydroxide.

6. The method of claim 1, wherein the polar organic solvent is dimethylsulfoxide (DMSO).

7. The method of claim 1, wherein the reaction is carried out in a nitrogen, oxygen, or air atmosphere.

* * * * *